United States Patent [19]

Meyer

[11] 4,401,458
[45] Aug. 30, 1983

[54] NOVEL SUBSTITUTED BENZO-2-THIA-1,3-DIAZIN-4(3H)-ONE-2,2-DIOXIDES

[75] Inventor: Willy Meyer, Riehen, Switzerland

[73] Assignee: Ciba-Geigy Corporation, Ardsley, N.Y.

[21] Appl. No.: 323,019

[22] Filed: Nov. 19, 1981

[30] Foreign Application Priority Data

Nov. 24, 1980 [CH] Switzerland ............ 8659/80

[51] Int. Cl.³ .............. C07D 285/16; A01N 9/14
[52] U.S. Cl. .............................. 71/91; 544/11
[58] Field of Search ....................... 71/91; 544/11

[56] References Cited

U.S. PATENT DOCUMENTS 4,158,559  6/1979  Stubenranch et al. ............ 544/11
4,182,623  1/1980  Kloek ............................... 544/11
4,298,731 11/1981  Hamprecht et al. .............. 544/11

Primary Examiner—Jane T. Fan
Attorney, Agent, or Firm—Frederick H. Rabin

[57] ABSTRACT

The benzo-2-thia-1,3-diazin-4(3H)-one-2,2-dioxides of the formula I

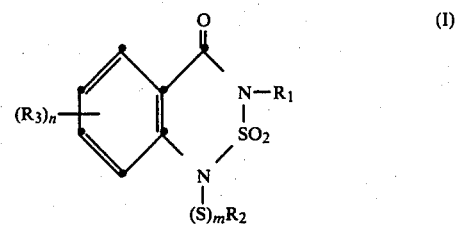

wherein $R_1$ is $C_1$–$C_6$-alkyl or $C_3$–$C_6$-cycloalkyl, $R_2$ is cyclopentyl which is unsubstituted or substituted by halogen or cyano, or it is $C_1$–$C_6$-alkyl which is substituted by cyano, hydroxyl, $C_1$–$C_4$-alkoxy, $C_1$–$C_4$-alkylthio, $C_1$–$C_4$-alkoxycarbonyl or $C_1$–$C_4$-alkylcarbonyloxy, $R_3$ is halogen, cyano, nitro, trifluoromethyl, $C_1$–$C_4$-alkyl or $C_1$–$C_4$-alkoxy, m is a number 1 or 2, and n is a number 0, 1 or 2, have herbicidal and plant-growth-regulating activity. They are suitable for selectively combating weeds in cultivated crops, particularly in soya-bean crops, in the post-emergence process, and for promoting root growth.

10 Claims, No Drawings

NOVEL SUBSTITUTED BENZO-2-THIA-1,3-DIAZIN-4(3H)-ONE-2,2-DIOXIDES

The present invention relates to novel substituted benzo-2-thia-1,3-diazin-3(4H)-one-2,2-dioxides having a herbicidal action and an action influencing plant growth, to processes for producing them, to herbicidal and plant-growth-regulating compositions which contain these benzo-2-thia-1,3-diazin-4)3H)-one-2,2-dioxides as active ingredients, and to the use thereof.

The novel substituted benzo-2-thia-1,3-diazin-4(3H)-one-2,2-dioxides correspond to the formula I

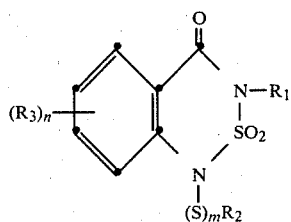

wherein $R_1$ is $C_1$–$C_6$-alkyl or $C_3$–$C_6$-cycloalkyl; $R_2$ is cyclopentyl which is unsubstituted or substituted by halogen or cyano, or it is $C_1$–$C_6$-alkyl which is substituted by cyano, hydroxyl, $C_1$–$C_4$-alkoxy, $C_1$–$C_4$ alkylthio, $C_1$–$C_4$-alkoxycarbonyl or $C_1$–$C_4$-alkylcarbonyloxy; $R_3$ is halogen, cyano, nitro, trifluoromethyl, $C_1$–$C_4$-alkyl or $C_1$–$C_4$-alkoxy; m is a number 1 or 2, and n is a number 0, 1 or 2.

In the compounds of the formula I, the alkyl groups can be straight-chain or branched-chain and they embrace all suitable forms, such as methyl, ethyl, n-propyl, isopropyl, n-butyl, isobutyl and sec- or tert-butyl, also the straight-chain and branched-chain variants of pentyl and hexyl.

The compounds of the formula I are novel. Benzo-2-thia-1,3-diazin-4-(3H)-one-2,2-dioxides having herbicidal activity are known, for example from the German Patent Specification No. 1,542,836, the German Offenlegungsschriften Nos. 2,443,901 and 2,656,289, or the U.S. Pat. Specif. No. 4,158,559. The present compounds are characterised by a substituted alkylmercapto group or an unsubstituted or substituted cycloalkylmercapto group on the nitrogen atom in the 1-position of the benzo-2-thia-1,3-diazin-4(3H)-one-2,2-dioxide molecule. The compounds have a good herbicidal action, and are especially suitable for selectively combating weeds in cultivated crops of soya bean.

It has also been established that the compounds of the formula I, when applied in small amounts as seed dressing, or when sprayed onto the field shortly after sowing, are able to promote the germination power and the root growth of seed. Compared with untreated seed, the treated seed is capable of bringing about within 10–30 days an acceleration of the growth of the fruit of up to 30%. Consequently, it is possible to cultivate certain crops even in climatically unfavourable regions where the summer is short, or to cultivate in a favourable climate a second crop by virtue of the shorter growth time. To be particularly emphasised however is the increase in root growth obtained with compounds of the formula I, especially with 1-(2-cyanoprop-2-yl-(sulfenyl)-3-isopropyl-benzo-2-thia-1,3-diazin-4(3H)-one-2,2-dioxide, in the case of cereals, in particular wheat.

The novel benzo-2-thia-1,3-diazin-4(3H)-one-2,2-dioxides are produced by reacting a benzo-2-thia-1,3-diazin-4(3H)-one-2,2-dioxide which is unsubstituted in the 1-position and corresponds to the formula II

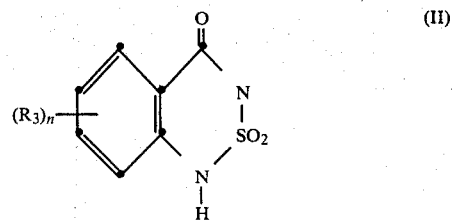

wherein n, $R_1$ and $R_3$ have the meanings defined under the formula I, in a suitable organic solvent or diluent, in the presence of an acid-binding agent, with an alkylsulfenyl halide of the formula III

wherein Hal is a chlorine or bromine atom, and $R_2$ and m have the meanings defined.

Suitable solvents or diluents for this reaction are organic agents inert to the reactants, for example tetrahydrofuran, dioxane, toluene or acetonitrile.

Acid-binding agents that can be used are inorganic or organic bases, alkali metal alcoholates, carbonates or bicarbonates of alkali metals and alkaline-earth metals, and secondary or tertiary amines. The agents are used in equimolecular amounts with the alkylsulfenyl halide of the formula III.

The production of the benzo-2-thia-1,3-diazin-4(3H)-one-2,2-dioxides of the formula II is known, and is described for example in the German Patent Specification No. 1,542,836 or in the German Offenlegungsschriften Nos. 2,443,901 and 2,656,289. They can be produced for example by cyclisation of N-alkyl-N'-[2-(carboxyl)-phenyl]-sulfoneamides of the formula

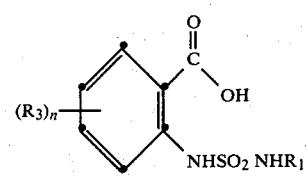

wherein n, $R_1$ and $R_3$ have the given meanings, by means of condensation agents. Suitable condensation agents are acid chlorides, such as phosphorus oxychloride or thionyl chloride.

The alkylsulfenyl halides of the formula (III) are likewise known compounds. They are obtained for example by reaction of alkanedisulfides with chlorine or with sulfuryl chloride.

The compounds of the formula I are stable and are soluble in the customary organic solvents, such as alcohols, ethers, ketones, dimethylsulfoxide and dimethylformamide. They have relatively low toxicity, and they can be handled and processed with just the usual precautionary measures.

Preferred compounds of the formula I are those in which $R_1$ is a $C_1$–$C_4$-alkyl group, $R_2$ is a $C_1$–$C_5$-alkyl group which is substituted by cyano or $C_1$–$C_4$-alkoxycarbonyl, or it is a cyclopentyl group which is substituted by chlorine or cyano, R₃ is chlorine, n is nought or 1, and m is 1 or 2.

Compounds of most interest in this preferred group of compounds are those in which $R_2$ is a $C_1$-$C_5$-alkyl group substituted by cyano, n is nought, and m is 1, and compounds amongst these to be particularly emphasised are those in which $R_2$ is a $C_1$-$C_5$-alkyl group substituted by cyano, corresponding to —$C(C_1$-$C_2$-alkyl$)_2$CN.

The active ingredients or the compositions containing them can be applied before emergence of the plants on sown cultivated areas (pre-emergence), but they are preferably applied as "contact herbicides" to the weed-infested cultivated crops after emergence of the plants (post-emergence). In applied amounts of 0.5 to 5 kg of active ingredient per hectare, a marked herbicidal effect on the weed flora is achieved, whilst the cultivated plants, particularly soya bean, remain unaffected.

The compositions according to the invention are produced in a manner known per se by the intimate mixing and grinding of active ingredients of the general formula I with suitable carriers and/or distributing agents, optionally with the addition of antifoaming agents, wetting agents, dispersing agents and/or solvents, all inert to the active ingredients. The active ingredient can be obtained and used in the following forms:

solid preparations: dusts, scattering agents, granulates (coated granules, impregnated granules and homogeneous granules);

water-dispersible concentrates of active ingredient: wettable powders, pastes, emulsions or emulsion concentrates, and liquid preparations: solutions and dispersions.

The concentration of active ingredient in the compositions according to the invention is 1 to 80 percent by weight, and when being applied the compositions can if necessary contain the active ingredient also at low concentrations, for example at about 0.05 to 1% by weight.

Other biocidal active substances or compositions can be mixed with the described compositions according to the invention. The novel compositions can thus contain, in addition to the stated compounds of the formula (I), for example insecticides, fungicides, bactericides, fungistatics, bacteriostatics or nematocides, or further herbicides, in order to broaden their sphere of action.

The Examples which follow describe in detail the production of the active ingredients and of the herbicidal compositions according to the invention. The temperature values in the Examples are given in degrees Centigrade, 'parts' and percentages are by weight, and pressure values are given in millibars (mbars).

EXAMPLE 1

Production of 1-(2-cyanoprop-2-yl-sulfenyl)-3-isopropyl-benzo-2-thia-1,3-diazin-4(3H)-one-2,2-dioxide.

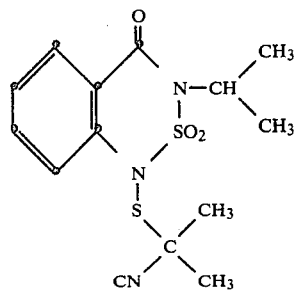

200 g of 3-(isopropyl)-1H-benzo-2-thia-1,3-diazin-4(3H)-one-2,2-dioxide are dissolved in 1000 ml of dioxane. To this solution are added, with stirring and cooling, 100 g of potassium tert-butylate dissolved in 1000 ml of tetrahydrofuran. The mixture is evaporated to dryness, and the solid residue is dissolved again in 1000 ml of tetrahydrofuran. There are then added to this solution, with stirring and cooling, 110 g of 2-cyanoprop-2-yl-sulfenyl chloride. After a brief stirring at room temperature, the suspension obtained is diluted with 5000 ml of absolute ether, and filtration is finally performed to clear the solution. The solvent is evaporated off, and the residue is crystallised under petroleum ether to thus obtain 215 g of the title compound as a granular powder having a melting point of 102°–104° C.

The following compounds are obtained in an analogous manner:

| Comp.No. | $R_1$ | $(S)_mR_2$ | $(R_3)_n$ | Physical data |
|---|---|---|---|---|
| 1 | $C_3H_7$iso | $SC(CH_3)_2CN$ | — | m.p. 102–104° |
| 2 | $C_3H_7$iso | $SC(C_2H_5)_2CN$ | — | |
| 3 | $C_3H_7$iso | $SC(CH_3)(C_2H_5)CN$ | — | |
| 4 | $C_3H_7$iso | $SC(CH_3)_2COOC_2H_5$ | — | |
| 5 | $C_3H_7$iso | S—⟨ring⟩—Cl | — | |
| 6 | $CH_3$ | $SC(CH_3)_2CN$ | — | |
| 7 | $C_2H_5$ | $SC(CH_3)_2CN$ | — | |
| 8 | $C(CH_3)_3$ | $SC(CH_3)_2CN$ | — | |
| 9 | $C_2H_5$ | $SC(CH_3)_2CN$ | 6-Cl | |
| 10 | $C_3H_7$iso | S—⟨ring⟩—CN | — | 94°–96° C. |
| 11 | $C_3H_7$iso | $SSC(CH_3)_2CN$ | — | m.p. 106–108° |

EXAMPLE 2

Production of some preparations

Granulate

The following substances are used to produce a 5% granulate:

- 5 parts of 1-(2-cyanoprop-2-yl-sulfenyl)-3-isopropyl-benzo-2-thia-1,3-diazin-4(3H)-one-2,2-dioxide,
- 0.25 part of epoxidised vegetable oil,
- 0.25 part of cetyl polyglycol ether,
- 3.50 parts of polyethylene glycol, and
- 91 parts of kaolin (particle size: 0.3–0.8 mm).

The active substance is mixed with the epoxidised vegetable oil and dissolved in 6 parts of acetone, and the polyethylene glycol and cetyl polyglycol ether are then added. The solution obtained is sprayed onto kaolin and the acetone is subsequently evaporated off in vacuo.

Wettable powder

The following constituents are used to produce a) a 70% wettable powder and b) a 10% wettable powder:

(a)
- 70 parts of 1-(2-cyanoprop-2-yl-sulfenyl)-3-isopropyl-benzo-2-thia-1,3-diazin-4(3H)-one-2,2-dioxide,
- 5 parts of sodium dibutyl-naphthalene sulfonate,
- 3 parts of naphthalenesulfonic acid/phenolsulfonic acid/formaldehyde condensate (3:2:1),
- 10 parts of kaolin, and
- 12 parts of Champagne chalk;

(b)
- parts of the above active ingredient,
- 3 parts of a mixture of the sodium salts of saturated fatty alcohol sulfates,
- 5 parts of a naphthalenesulfonic acid/formaldehyde condensate, and
- 82 parts of kaolin.

The active ingredient is absorbed onto the appropriate carriers (kaolin and chalk), and the material is then mixed and ground with the remaining constituents. Wettable powders having excellent wetting and suspension properties are obtained. It is possible to obtain from wettable powders of this type, by dilution with water, suspensions containing from 0.1 to 8% of active ingredient, these suspensions being suitable for combating weeds in crops of cultivated plants.

Paste

The following substances are used to produce a 45% paste:

- 45 parts of the above active ingredient,
- 5 parts of sodium aluminum silicate,
- 14 parts of cetyl polyglycol ether with 8 mols of ethylene oxide,
- 1 part of oleyl polyglycol ether with 5 mols ethylene oxide,
- 2 parts of spindle oil,
- 10 parts of polyethylene glycol, and
- 23 parts of water.

The active ingredient is intimately mixed and ground with the additives in suitable apparatus. There is obtained a paste from which suspensions of the concentration required can be prepared by dilution with water.

Emulsion concentrate

The following constituents are mixed together to produce a 25% emulsion concentrate:

- 25 parts of the above active ingredient,
- 5 parts of a mixture of nonylphenolpolyoxyethylene and calcium dodecylbenzene sulfonate,
- 15 parts of cyclohexanone, and
- 55 parts of xylene.

This concentrate can be diluted with water to give emulsions of suitable concentration, for example 0.1 to 10%.

EXAMPLE 3

Herbicidal action with application of the active ingredients after emergence of the plants (post-emergence)

Various cultivated plants and weeds are grown from seed in pots in a greenhouse until they have reached the 4- to 6-leaf stage. The plants are they sprayed with aqueous active-ingredient emulsions (obtained from the 5% emulsion concentrate) in different dosages. The treated plants are subsequently kept under optimum conditions of light, watering, temperature (22°–25° C.) and relative humidity (50–70%). The evaluation of the tests is made 15 days after the treatment of the test plants. The compound No. 1 exhibited in this test a strong herbicidal action.

Promotion of germination

In order to determine the action promoting germination, the test compounds are sprayed as aqueous emulsions (obtained by dilution of the 25% emulsion concentrate) onto wheat seeds, the amount applied being 25 mg per kg of seed. The seen treated in this manner is then sown in normal garden soil in a greenhouse. The seedlings aree grown in a climatic chamber under controlled subtropical conditions. The shoots are cut off level with the soil after 30 days, and the fresh weight is compared with that of shoots grown from untreated wheat seed under the same conditions.

The wheat shoots treated with the compound No. 1 show a 21% increase in weight compared with that of the shoots from untreated wheat seed.

Root growth

In order to determine the promotion of root growth, wheat seed which has been dressed with 25 mg of active ingredient (compound No. 1) per kg of seed, as well as untreated wheat seed of the same variety, are sown in flat plastics cylinders (5 cm × 30 cm), 10 seeds being sown in each cylinder. The cylinders are then kept in climatic chambers under controlled conditions. The seedlings are carefully washed from the soil after 10 days. The length of the roots and their dry weight are determined and the values compared with those obtained from seedlings of the untreated wheat.

The seedlings treated with the compound No. 1 have in this test a growth in length increased by 18% and a 15% higher dry weight of the roots.

To determine the promotion of root growth, wheat seed is sown in flat plastics cylinders filled with soil (5 cm × 30 cm), 10 seeds being sown in each cylinder. Immediately after sowing, the test substances are applied, as a 25% active-ingredient formulation, to the soil, the amounts applied corresponding respectively to 0.3 and 1 kg of active ingredient per hectare. The cylinders are then kept in climatic chambers under controlled conditions. The seedlings are gently freed from adhering soil by careful washing after 10 days. The length of the roots is subsequently measured and compared with values obtained from the untreated control specimens. The results are listed in the following Table, those given by substance A, namely 3-isopropyl-(1H)- benzo-2,1,3-thiadiazin-4-one-2,2-dioxide, serving as a comparison.

| Applied amount | Length of the roots in % of the control compound | |
| --- | --- | --- |
| kg/hectare | A | I |
| 0.3 | 98 | 116 |
| 1.0 | 93 | 112 |

The results show that the effect which the compound No. 1 according to the invention has on root growth is substantially more favourable that that of the comparative substance A.

What is claimed is:

1. A compound of the formula:

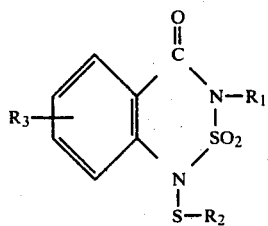

wherein $R_1$ is alkyl of 1 to 4 carbon atoms;

$R_2$ is 2-cyanoprop-2-yl, 2-cyanobut-2-yl, 3-cyanopent-3-yl or 2-cyanocyclopentyl; and $R_3$ is hydrogen or chloro.

2. A compound according to claim 1 wherein $R_3$ is hydrogen.

3. 1-(2-Cyanoprop-2-yl-sulfenyl)-3-isopropyl-benzo-2-thia-1,3-diazin-4(3H)-one-2,2-dioxide.

4. The method of selectively combatting weeds in cultivated crops which comprises applying to the weeds or to the locus of their growth a herbicidally effective amount of a compound according to claim 1.

5. The method of claim 4 wherein said compound is 1-(2-cyanoprop-2-ylsulfenyl)-3-isopropylbenzo-2-thia-1,3-diazin-4(3H)-one-2,2-dioxide.

6. The method of claim 4 wherein the crop is soya bean.

7. The method of regulating the growth of cultivated plants by increasing root growth which comprises applying to the seeds of the plant an effective amount of a compound according to claim 1.

8. The method of claim 7 wherein said compound is 1-(2-cyanoprop-2-ylsulfenyl)-3-isopropylbenzo-2-thia-1,3-diazin-4(3H)-one-2,2-dioxide.

9. The method of claim 7 wherein the cultivated plant is wheat.

10. A composition comprising a quantity of a compound according to claim 1 at least sufficient to effect a plant growth regulating or herbicidal response, in combination with an inert carrier therefor.

* * * * *